US010583046B2

(12) United States Patent
Wilson et al.

(10) Patent No.: US 10,583,046 B2
(45) Date of Patent: Mar. 10, 2020

(54) COMPRESSION GARMENTS AND USES THEREOF

(71) Applicants: Eric Wilson, Coopersburg, PA (US); David Salisbury, Gettysburgh, PA (US)

(72) Inventors: Eric Wilson, Coopersburg, PA (US); David Salisbury, Gettysburgh, PA (US)

( * ) Notice: Subject to any disclaimer, the term of this patent is extended or adjusted under 35 U.S.C. 154(b) by 700 days.

(21) Appl. No.: 15/235,768

(22) Filed: Aug. 12, 2016

(65) Prior Publication Data

US 2017/0280789 A1  Oct. 5, 2017

Related U.S. Application Data

(60) Provisional application No. 62/203,941, filed on Aug. 12, 2015.

(51) Int. Cl.
*A61F 13/08* (2006.01)
*A61F 5/01* (2006.01)

(52) U.S. Cl.
CPC ............ *A61F 13/085* (2013.01); *A61F 13/08* (2013.01); *A61F 5/01* (2013.01)

(58) Field of Classification Search
CPC .......... A61F 13/085; A61F 13/08; A61F 5/01; A61F 5/06; A61F 13/06; A41D 13/00; A41D 27/24; A41D 1/06; A41D 2500/20; A41B 11/003; A41B 11/08; A41B 11/00; A41B 1/08; A41B 2400/38; A41H 43/00; D03D 1/00; D03D 15/08
USPC ........................................................ 602/60
See application file for complete search history.

(56) References Cited

U.S. PATENT DOCUMENTS

| | | | |
|---|---|---|---|
| 2,574,873 A | 5/1949 | Jobst et al. |
| 3,470,568 A | 10/1969 | Belkin |
| 3,942,525 A | 3/1976 | Dragan et al. |
| 4,215,687 A | 8/1980 | Shaw |
| 4,878,504 A | 11/1989 | Nelson |
| 5,005,567 A | 4/1991 | Gilman et al. |
| 5,520,630 A | 5/1996 | Daneshvar et al. |
| 5,653,244 A | 8/1997 | Shaw |
| 6,216,495 B1 | 4/2001 | Couzan et al. |
| 6,311,334 B1 | 11/2001 | Reinhardt et al. |
| 6,338,723 B1 | 1/2002 | Carpenter et al. |
| 6,520,926 B2 | 2/2003 | Hall |
| 6,613,007 B1 | 9/2003 | Reid et al. |
| 6,673,421 B1 | 1/2004 | Andrews et al. |
| 6,684,412 B2 | 2/2004 | Ricci et al. |
| 7,028,690 B2 | 4/2006 | Schneider et al. |
| 7,270,642 B2 | 9/2007 | Ouchene et al. |
| 7,329,232 B2 | 2/2008 | Lipshaw et al. |
| 7,562,541 B2 | 7/2009 | Hermanson et al. |
| 7,942,838 B2 | 5/2011 | Farrow et al. |
| 8,034,013 B2 | 10/2011 | Winkler et al. |
| 8,083,110 B2 | 12/2011 | Wilkens |
| 8,162,869 B2 | 4/2012 | Graham |

(Continued)

FOREIGN PATENT DOCUMENTS

WO   2014105676 A1   7/2014

OTHER PUBLICATIONS

FarrowMed Innovative Medical Solutions (brochure).

(Continued)

*Primary Examiner* — Tarla R Patel
(74) *Attorney, Agent, or Firm* — Patrick J. Halloran

(57) ABSTRACT

This disclosure relates to the field of compression garments and uses thereof.

14 Claims, 5 Drawing Sheets

(56) References Cited

U.S. PATENT DOCUMENTS

| | | | |
|---|---|---|---|
| 8,221,340 | B2 | 7/2012 | Farrow et al. |
| 8,235,923 | B2 | 8/2012 | Avitable et al. |
| 8,251,933 | B2 | 8/2012 | Farrow et al. |
| 8,317,736 | B2 | 11/2012 | Virkus et al. |
| 8,491,514 | B2 | 7/2013 | Creighton et al. |
| 8,632,840 | B2 | 1/2014 | Avitable et al. |
| 8,641,653 | B2 | 2/2014 | Winkler et al. |
| 8,740,828 | B2 | 6/2014 | Brown et al. |
| 8,777,886 | B2 | 7/2014 | Mueller et al. |
| 8,808,210 | B2 | 8/2014 | Farrow et al. |
| D724,307 | S | 3/2015 | Keeffe et al. |
| 9,566,206 | B2 | 2/2017 | Leonard et al. |
| 2004/0111048 | A1 | 6/2004 | Jensen et al. |
| 2006/0020236 | A1 | 1/2006 | Ben-Nun et al. |
| 2007/0161933 | A1 | 7/2007 | Ravikumar |
| 2008/0249444 | A1 | 10/2008 | Avitable et al. |
| 2010/0056973 | A1 | 3/2010 | Farrow et al. |
| 2010/0168636 | A1 | 7/2010 | Allard |
| 2010/0312160 | A1* | 12/2010 | Creighton ............... A61F 13/10 602/62 |
| 2011/0125183 | A1* | 5/2011 | Lipshaw ............... A61F 13/085 606/201 |
| 2012/0102613 | A1 | 5/2012 | Loth et al. |
| 2012/0179084 | A1 | 7/2012 | Lipshaw et al. |
| 2012/0316480 | A1* | 12/2012 | Nolan ................... A61F 13/085 601/151 |
| 2013/0283500 | A1 | 10/2013 | Lipshaw et al. |
| 2013/0296763 | A1 | 11/2013 | Farrow et al. |
| 2013/0319128 | A1 | 12/2013 | Richardson et al. |
| 2014/0075781 | A1 | 3/2014 | Davis et al. |
| 2014/0081187 | A1 | 3/2014 | Wyatt et al. |
| 2014/0303533 | A1 | 10/2014 | Zeutzius et al. |
| 2015/0011922 | A1 | 1/2015 | Toth et al. |
| 2015/0025424 | A1 | 1/2015 | Richardson et al. |
| 2015/0051523 | A1 | 2/2015 | Lipshaw et al. |
| 2015/0051552 | A1 | 2/2015 | Lipshaw et al. |
| 2015/0073317 | A1 | 3/2015 | Wesley |
| 2015/0112380 | A1 | 4/2015 | Heller et al. |
| 2015/0245976 | A1 | 9/2015 | Jackson et al. |
| 2016/0058623 | A1 | 3/2016 | Lipshaw et al. |
| 2017/0273830 | A1* | 9/2017 | Hitschmann ........... A61F 5/0109 |

OTHER PUBLICATIONS

110% Double Life Shin/Calf Sleeves. Outside Magazine (Oct. 2014).

Ben, et al. Human Skin Wounds: A Major and Snowballing Threat to Public Health and the Economy. Wound Repair Regen. 17(6): 763-771 (2009).

Spentzouris, G. The Evaluation of Lower-Extremity Ulcers. Semin. Int. Radiol. 26: 286-295 (2009).

FarrowWrap Better Compression Made Simple (brochure dated Jan. 21, 2013).

Is this how your start your day? JuxtaLite (brochure (2012)).

CFR—Code of Federal Regulations Title 21, Sec. 890.5760 (Sep. 1, 2014).

* cited by examiner

US 10,583,046 B2

COMPRESSION GARMENTS AND USES THEREOF

RELATED APPLICATIONS

This application claims priority to U.S. Ser. No. 62/203,941 filed Aug. 12, 2015.

FIELD OF THE DISCLOSURE

This disclosure relates to the field of compression garments and uses thereof.

BACKGROUND OF THE DISCLOSURE

Currently available compression garments such as stockings, wraps and alternative devices are only effective when worn, and worn appropriately. There are numerous challenges to wearing such garments and most patients are therefore non-compliant with recommended therapy. Obstacles to proper compliance include obesity/body habitus, hand weakness, skin fraility, complexity of existing garments, pain and the inability to adjust the garments once applied, for instance. Many of the garments used today are associated with high cost, lack of warmth, hygiene/washability problems, the application of inconsistent pressure, durability problems, comfortability issues and the inability of the user to adjust the garment. Commonly used devices include, for instance, compression stockings, non-elastic binders, pneumatic compression sleeves, ACE wraps, Tubigrip, and the like. Each presents the user with significant difficulties of use which results in insufficient compliance with medical advice. Thus, there is a need in the art for a compression garment that provides suitable compression and ease of use under a variety of conditions and methods for using the same. Such compression garments and methods are provided herein.

BRIEF DESCRIPTION OF THE DRAWINGS

FIG. 1A. First embodiment. FIG. 1B. Second embodiment. FIG. 1C. Third embodiment. FIG. 1D. Fourth embodiment.

FIG. 2A. Fifth embodiment. FIG. 2B. Sixth embodiment.

FIG. 3A. Seventh embodiment. FIG. 3B. Eighth embodiment. FIG. 3C. Ninth embodiment.

FIG. 4A. Exemplary design 4. FIG. 4B. Exemplary design 5. Hashed-marked areas indicate areas including adhesive and/or receiving materials. Numbering indicates pressure indicators.

FIG. 5A. Rectangular embodiment including subparts A, B, B1 and C. FIG. 5B. First trapezoidal embodiment including subparts A, B, B1 and C. FIG. 5C. Second trapezoidal embodiment: 1. Tacky Silicone/polymer one one side (toward skin) and stretchy silicone rubber on outside (opposite skin). 2. Thin, flexible, yet stiff wooden shim encapsulated in fabric/silicone coating. 3. Thickness and number of silicone/polymer strips can vary depending upon site/nature of compression garment.

SUMMARY OF THE DISCLOSURE

This disclosure relates to compression garment that provide suitable compression and ease of use under a variety of conditions and methods for using the same.

DETAILED DESCRIPTION

This disclosure relates to compression garment that provide suitable compression and ease of use under a variety of conditions and methods for using the same. In some embodiments, the compression garment comprises a support material having a central axis, first and second surfaces opposite one another, and at least one edge on each surface, at least one of said edges being a first edge comprising an adhesive material on the first or second surface thereof, extending toward the central axis; and, at least one of said edges being a second edge comprising a receiving material that adheres to the adhesive material extending from a second edge toward the central axis. The compression garment is typically affixed to a body part by wrapping the compression garment around the body part such that the adhesive material and the receiving material contact one another to form a reversible bond, thereby reversibly but stably affixing the compression garment to the body part. For instance, a compression garment may be positioned by allowing one adhesive edge of the garment to contact and, e.g., "stick", to the skin thereby maintaining its position with ease while the user wraps/applies the remaining portion of the compression garment. The user may then grip a first edge of the compression garment, wrap the same around the calf, and contact the first edge with a second edge (the first and second edges comprising an adhesive and/or receiving material) to form a bond between those edges, thereby reversibly affixing the compression garment to the calf. The compression garment thereby provides pressure upon the body part. The pressure applied may be increased or decreased by adjusting how tightly the compression garment is wrapped around the body part (e.g., limb). This may be accomplished by the user by "feel", by the inclusion of a marking on the garment provided by, for instance, a health care practicioner such as a doctor, and/or by using a particular material that applies appropriate amount of pressure (e.g., having a particular type of weave). In some embodiments, then, methods for compressing a limb by wrapping the compression garment around the limb are also provided. In some embodiments, the compression garment provides a user-selected amount of pressure to the limb, meaning the pressure is selected by either the medical professional or user per se.

Figure 1A:
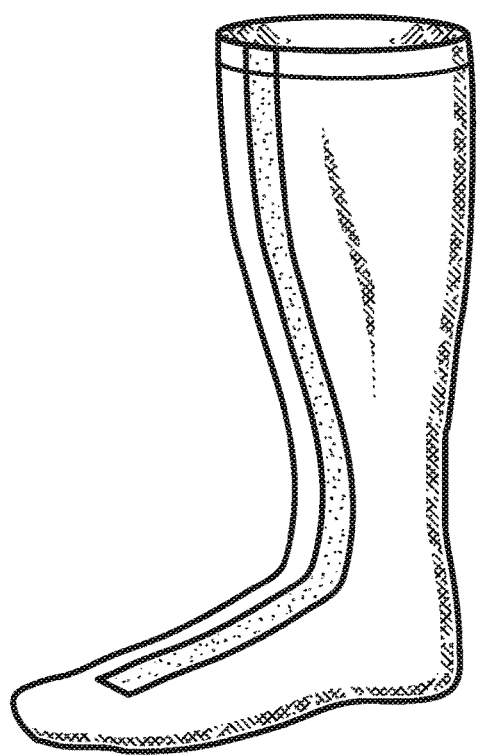
FIGS. 1A-D. Exemplary compression garments. Hashed-marked areas indicate areas including adhesive and/or receiving materials.
Figure 1B:
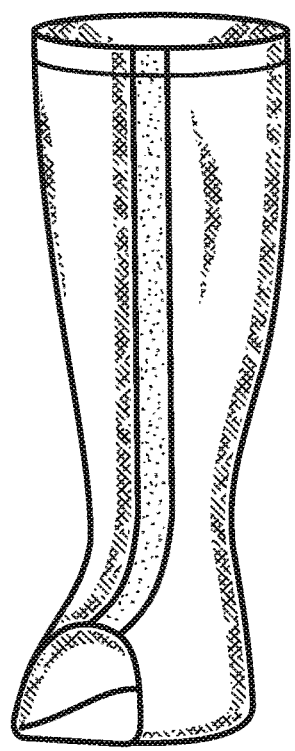
Figure 1C:
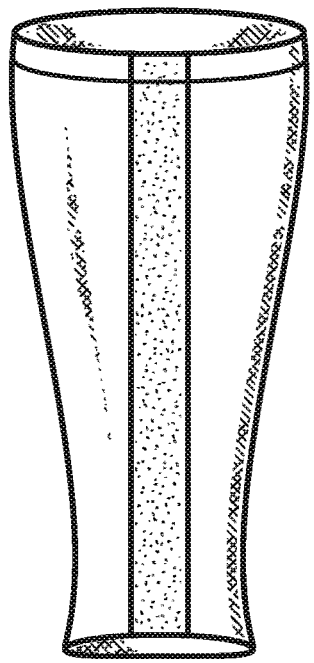
Figure 1D:
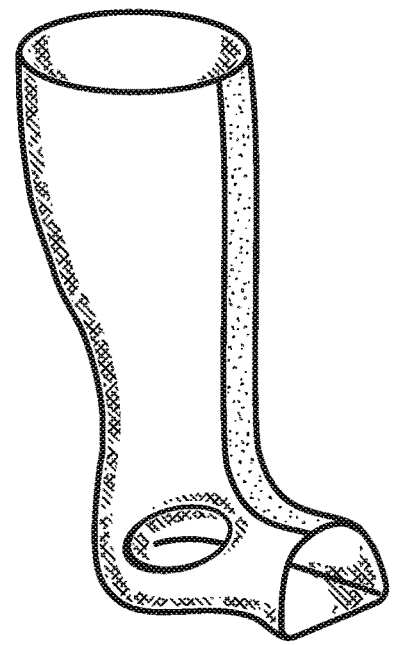
Figure 2A:
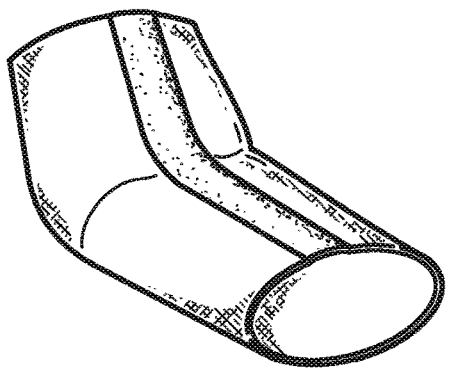
FIGS. 2A-B. Additional exemplary compression garments. Hashed-marked areas indicate areas including adhesive and/or receiving materials.
Figure 2B:
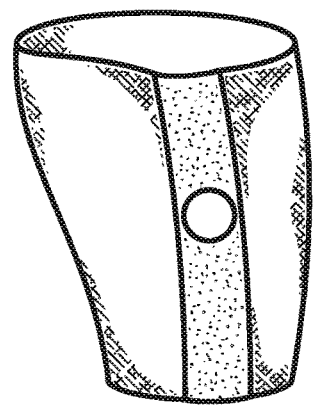
Figure 3A:
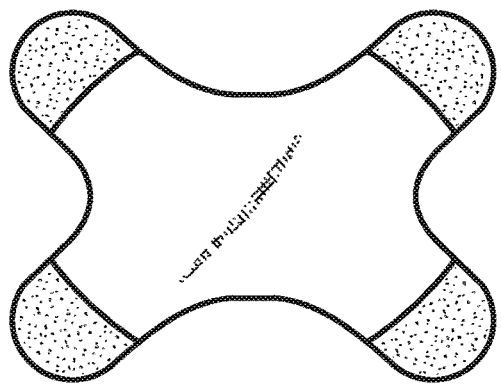
FIGS. 3A-C. Additional exemplary compression garments. Hashed-marked areas indicate areas including adhesive and/or receiving materials.
Figure 3B:
Figure 3C:
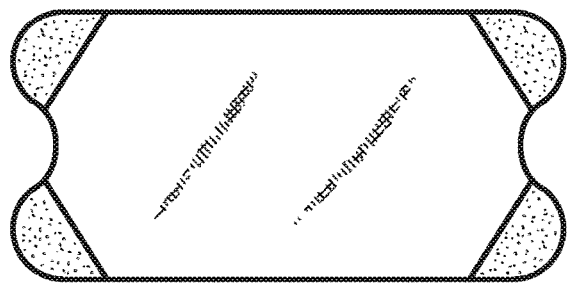
Figure 4A:
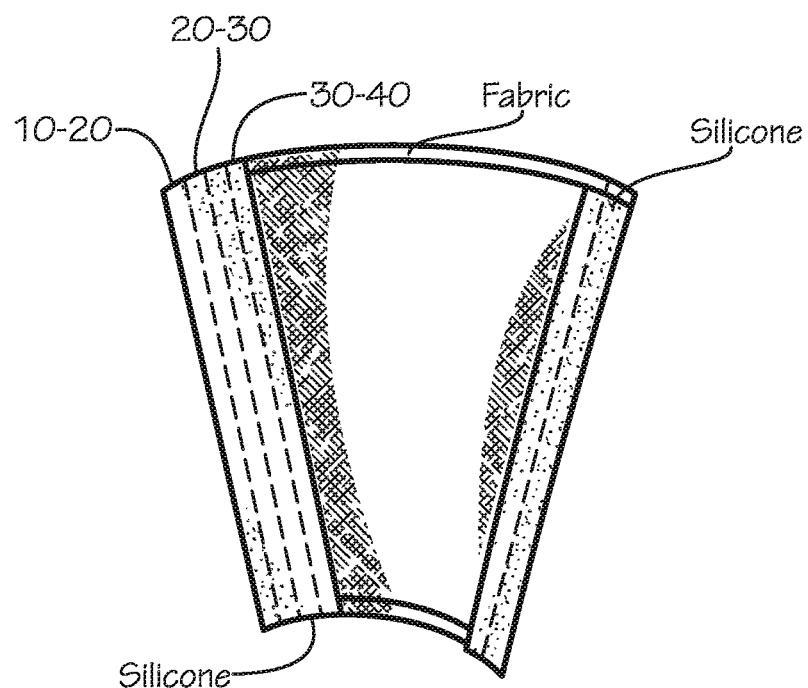
FIGS. 4A-B. Exemplary compression garments.
Figure 4B:
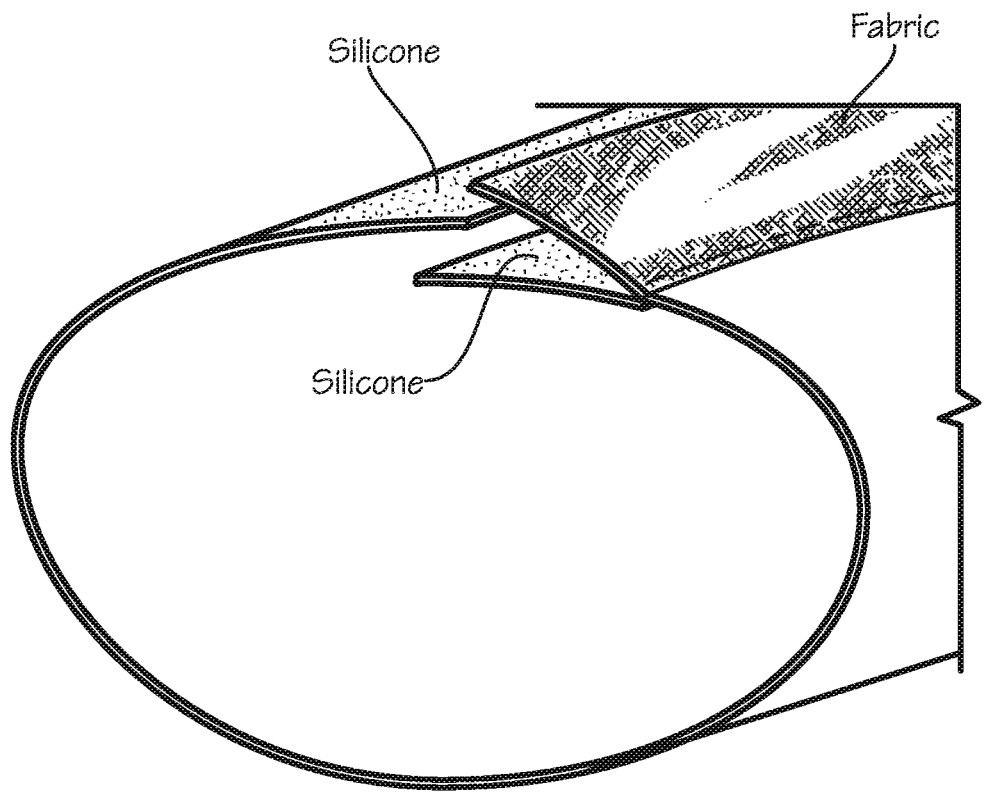

The compression garment may be produced in any suitable form and/or shape. For instance, the compression garment may take any of the forms and/or shapes illustrated in FIGS. 1A-D. For instance, in some embodiments, the compression garment may be suitable for wrapping around a body part such as the foot, calf, thigh, torso, neck, upper arm, lower arm, elbow, and/or any portion thereof. In some embodiments, the compression garment may wrap around the foot with or without also covering one or more toes and/or the heel of the foot. For instance, the compression garment may also be suitable for wrapping around the calf. The compression garment may cover the entire calf area (i.e., from the ankle to just below the knee) or a part thereof. A compression garment for the elbow would typically extend onto at least part of the upper and/or lower arm. In some embodiments, the compression garment may simply form a "wrap" in which one edge (e.g., comprising an adhesive material) is bound to the body part and another edge (e.g., comprising a receiving material) is gripped and stretched around the body part until the same makes contact with another adhesive edge or portion of the garment. In some embodiments, that other edge or portion may comprise a receiving material as described herein. The compression garment thereby applies pressure to the body part, which may be adjusted by tightening or loosening how tightly the compression garment is wrapped upon the body part. In another exemplary embodiment, the compression garment may include a flap that together with a first edge of the support material forms a receptacle for a second edge of the support material (FIGS. 2A-B). Under this construction, the underside of the flap and the upper surface of the first edge may comprise adhesive materials (the same or different) and the second edge may comprise receiving material on one or both surfaces (e.g., the upper and lower surfaces thereof). In use, the second edge may be secured to the flap/first edge structure through the adhesive and receiving materials.

The compression garments described herein may take the form of compression stockings, non-elastic binders, pneumatic compression sleeves, ACE wraps, Tubigrips, and the like. Exemplary forms and/or shapes in which the compression garment described herein may be fabricated include, for instance, any of those described in U.S. Pat. Nos. 2,574,873; 3,942,525; 4,878,504; 6,216,495B1; 6,311,334B1; 6,673, 421B1; 6,684,412B2; 7,028,690B2; 7,562,541B2; 7,942, 838B2; 8,221,340B2; 8,235,923B2; 8,251,933B2; 8,317, 736B2; 8,491,514B2; 8,632,840B2; 8,641,653B2; 8,740, 828B2; 8,777,886B2; 8,808,210B2; D724,3075; U.S. Pat. Pub. No. 2012/0102613A1; and/or 2015/0051523A1. In some embodiments, such forms and/or shapes may be fabricated to include the adhesive/receiving materials as described herein. In some embodiments, the attachment mechanisms described therein may be replaced, completely or partially, with the adhesive material/receiving materials described herein. Other embodiments are also contemplated as would be understood by those of ordinary skill in the art.

The compression garment typically includes at least one adhesive material and at least one receiving material. One of the adhesive materials may bond to the skin to reversibly affix the same thereto while the garment is placed upon the body part. This adhesive material that bonds to the skin may be referred to as a second adhesive material and may be the same or different from the adhesive material used to secure one edge of the compression garment to another edge in order to affix the garment to the body part. The adhesive and/or receiving materials may be present as continuous border or intermittently along the outer perimeter of the garment or may be present only on certain portions of the garment (e.g., the corners, FIGS. 1A-D). In some embodiments, the adhesive and/or receiving materials may also be present as continuous and/or discontinuous strips or segments of various geometry (e.g., shapes) on the garment equidistant from the central axis or, in other embodiments, less than or more than equidistant from the central axis.

Figure 5A:
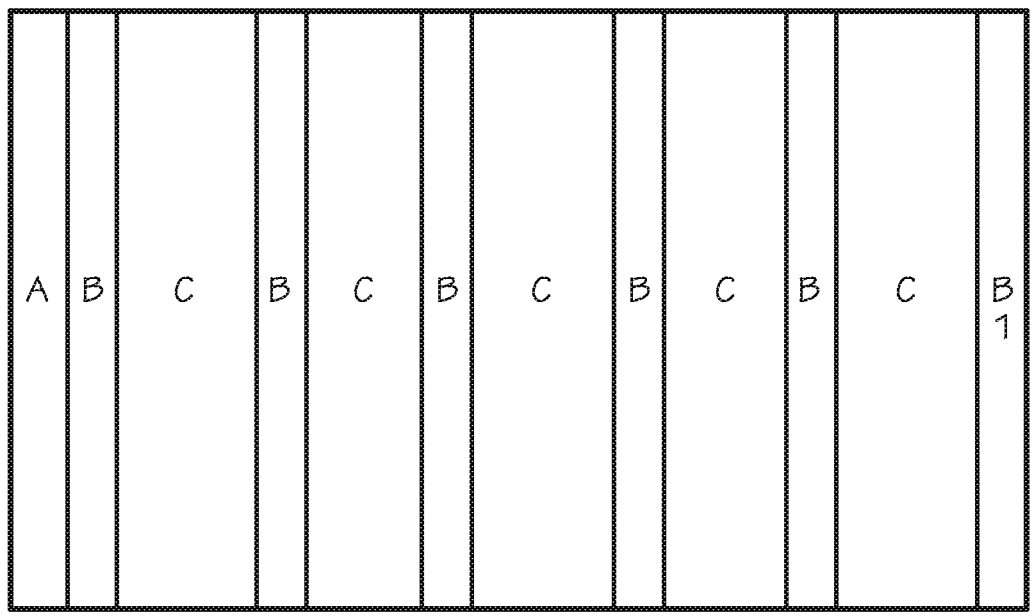
FIGS. 5A-C. Exemplary compression garment comprising alternating sections comprising or lacking, respectively, adhesive and/or receiving materials.
Figure 5B:
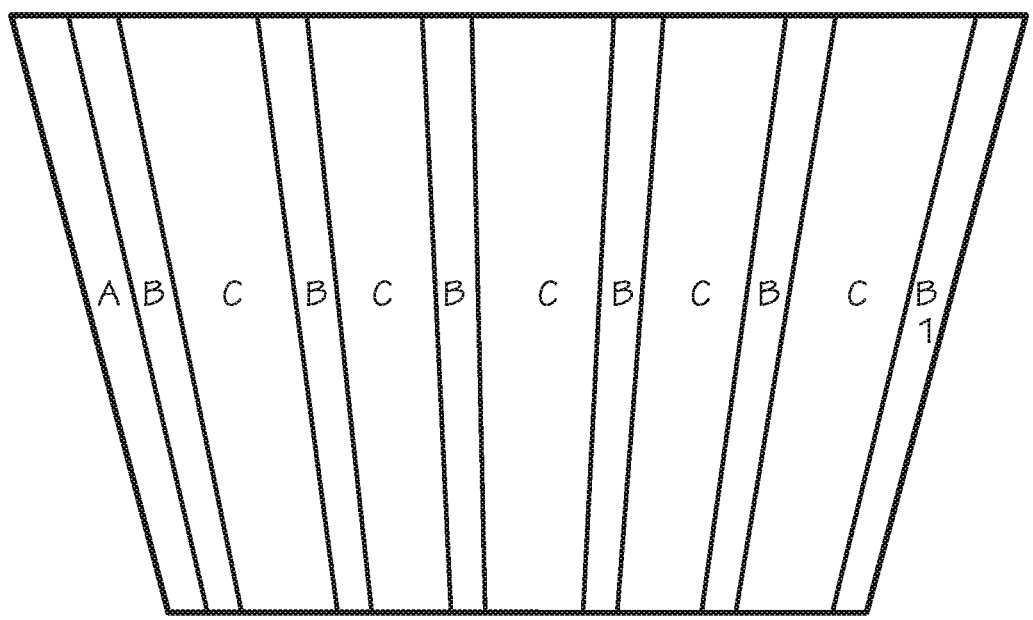
Figure 5C:
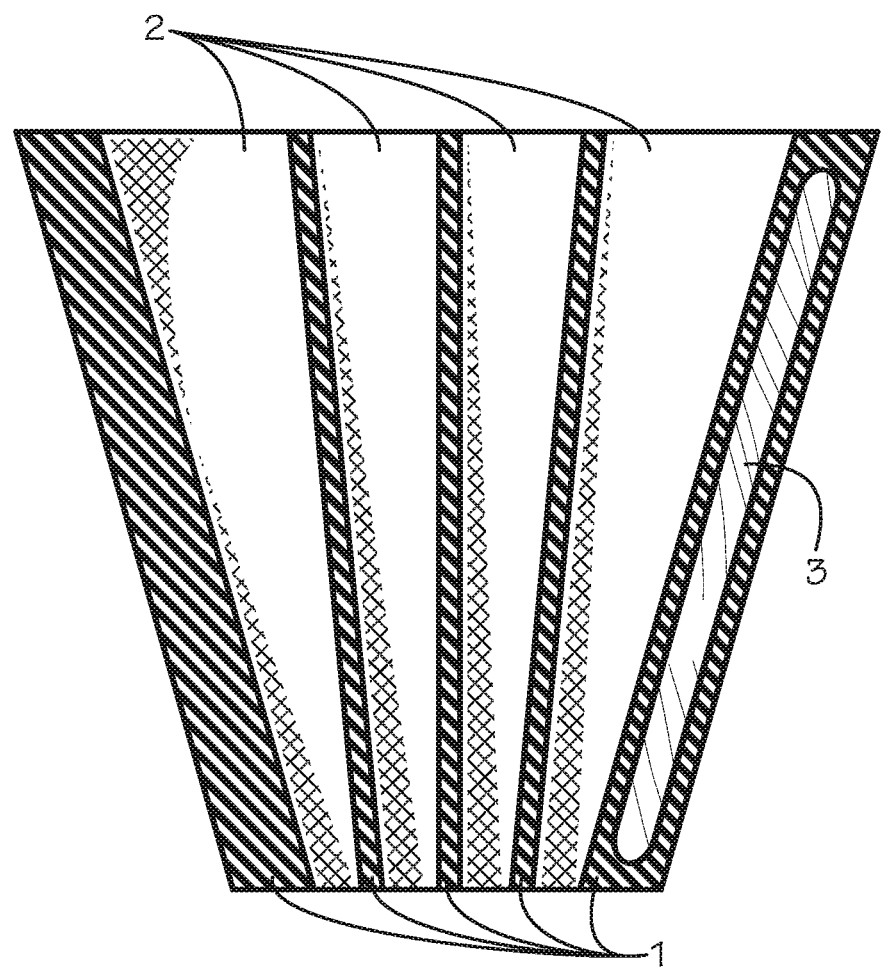

In some embodiments, the compression garment may comprise alternating sections comprising and lacking the adhesive and/or receiving material. Such embodiments are illustrated in FIGS. 5A-C. In each of FIGS. 5A and B, areas comprising adhesive and/or receiving material material on at least the surface of the garment immediately adjacent to the skin of the user (i.e., contacting the skin) are labeled B (and B1) and areas lacking adhesive and/or receiving material are labeled C. As shown in FIGS. 5A and B, such areas may extend from one edge to another edge of the compression garment. The adhesive and/or receiving material in areas containing the same may be in a continuous "layer", or may be discontinuously present in those areas (e.g., as subsections within a section in the shape of, e.g., a square, rectangle, triangle, circle (or dot)). The use of alternating areas including and lacking adhesive and/or receiving material provides for, among other advantages, ease of use, distribution of intersegmental pressure, improved breathability while not comprising positioning on the limb (e.g., slippage), and decreased material cost (e.g., the use of less adhesive material) in producing the compression garment. In preferred embodiments, the compression garment also includes a semi-rigid/rigid support (labeled A in FIGS. 5A and B) that may be used in applying the compression garment to the limb (e.g., wrapping it around the limb). For instance, the user may grip the semi-rigid/rigid support A while fitting the compression garment to the limb. The inclusion of alterating areas of adhesive and/or receiving material also provides for progressive adhesion of the compression garment as it is applied to (e.g., wrapped around) the limb. For instance, using FIG. 5A as an example, the user may begin the wrapping process by adhering area B1 of the compression garment to the skin and gripping semi-rigid/ rigid support A. The user may then simply wrap the compression garment around the limb by pulling on semi-rigid/ rigid support A. As the compression garment is wrapped about the limb, each successive section B comprising adhesive material will adhere to the skin in series (with respect to FIG. 5A and B in a right-to-left progression). In this way, the risk of slippage as the compression garment is being applied is decreased, thereby increasing the ease of use of this compression garment as compared to other currently available devices. The pressure applied by the garment may also remain applied in each section as the compression garment is wrapped around the limb. In addition, once in place, this compression garment provides improved breathability over one including adhesive and/or receiving material over the entire surface thereof. Rigid/semi-rigid support A may be comprised of any suitable material that may be gripped and subjected to pressure (e.g., as would be applied during the wrapping process) without breaking. It is preferred that rigid/semi-rigid support A run along the entire length of the edge of the compression garment which allows the user to grip the same anywhere along that edge during application and/or removal of the compression garment to/from the limb. Suitable materials may include natural products, for instance, wood. Rigid/semi-rigid support A may also be positioned upon, or encapsulated in, the adhesive and/or receiving material, and/or the support material. In such embodiments, rigid/semi-rigid support A should be comprised of a material that would bond sufficiently to the adhesive and/or receiving material. FIG. 5C illustrates another trapezoidal embodiment of the compression garment described herein. The embodiment of FIG. 5C includes alternating sections comprising and lacking, respectively an adhesive and/or receiving material. One of ordinary skill in the art may understand these alternating sections to be "strips" of adhesive material upon the support material. This embodiment also comprises a tackified adhesive material (e.g., the "Tacky Silicone/Polymer") on one surface of the support material (that which in use will be facing toward the skin of the limb being wrapped by the compression garment) and another material (e.g., a receiving material such as the "Stretchy Silcone Rubber" described therein on the surface of the compression garment facing away from the skin of the limb being wrapped. This embodiment shows this arrangement of materials to be present at a first edge of the compression garment (e.g., the left edge as illustrated in FIG. 5C). As noted in FIG. 5C, the thickness and number of silicone/polymer strips (e.g., the adhesive material) may vary depending upon the size and/or nature of the compression garment. The shape of such strips may also be varied as described herein. FIG. 5C also illustrates a second edge of the compression garment, opposite the first edge, that may comprise a similar arrangement of materials (i.e., tacky silicone/polymer and stretchy silicone rubber), but also comprises a sufficiently stiff but flexible (e.g., semi-rigid) support as a wooden shim encapsulated in fabric and/or the silicone material. This embodiment provides the same advantages as described in FIG. 5A-B, namely, among other advantages, ease of use, distribution of intersegmental pressure, improved breathability while not comprising positioning on the limb (e.g., slippage), and decreased material cost (e.g., the use of less adhesive material) in producing the compression garment. Variations of such embodiments, such as the use of other materials may also be suitable as would be understood by those of ordinary skill in the art.

As described above, the compression garment comprises a support material. In some embodiments, the support material may comprise: stretch characteristics; a textile material; a compressible material; a non-compressible material; an elastic material; an inelastic material; elastic compression threads; elastomeric loop material; elastomeric fabric; a semi-compressible elastomeric material; woven material; non-woven material; a rhombic lattice pattern; longitudinal yarns arranged to form a fabric having a length and generally parallel to the length, and a plurality of transverse elastomeric yarns connecting adjacent longitudinal yarns and about equally spaced about a length of the longitudinal yarns where, in a stretched state, the longitudinal yarns are spaced from one another and remain generally parallel to the length; a seamlessly attached antislip coating along one or more edges; breathable material; breathable short stretch foam laminate material; a wicking layer; measurement indicia; pressure indicia; an arrangement of materials to provide graduated compression along its length; padding; a compressible or semi-compressible liner; a medicinal agent, a therapeutic agent, or a a medicinal agent and a therapeutic agent; and/or an inner and outer compressible and/or non-compressible layer upon either or both of which is a compressible layer. In combination with the adhesive and/or receiving materials, the compression garment may present as a single layer that does not require, e.g., additional adhesive layers such as a polyurethane as is common in the art. In some such embodiments, the support material is a single, open mesh, breathable, stretchable, elastomeric fabric substrate (e.g., Spandex, Lycra, nylon and/or the like) that bonds (e.g., directly) to and/or is encapsulated by the adhesive and/or receiving material. Other materials may also be suitable, as would be understood by those of ordinary skill in the art.

The compression garment typically comprises both adhesive and receiving materials. The adhesive and receiving materials interact with one another to secure the compression garment upon a body part such as a limb. Thus, the compression garment typically includes an adhesive material on one edge and receiving material on another edge, where the edges are folded upon one another in order to secure and/or wrap the compression garment upon the body part. In some embodiments, the adhesive and receiving materials may be present on first and second surfaces of, respectively, of the support material such that the materials interact with one another upon wrapping around the limb (e.g., calf) to securely affix the compression garment around the body part. The adhesive and receiving materials form a reversible but stable bond with each other, thereby securing the first surface to the second surface. By "stable" is meant a bond through or with which the compression garment is affixed to the body part for a period of time (e.g., about any of 5, 10, 15, 20, 25, 30, 45, 60 minutes or more), absent a physical dislocation of one from the other. A "stable" bond is also one that is maintained in the presence of heat (e.g., average normal human or animal body temperature ±10%), moisture/humidity (e.g., water, sweat, any of about 10, 20, 30, 40, 50, 60, 70, 80, 90 or 100% humidity), cold (e.g., to any of about 0 to about 30° C.), and/or other conditions. The compression garment may be washable in a standard washing machine and may, for instance, survive about five or more wash cycles. It is preferred that the compression garment may be hand-washable in a standard soapy/detergent solution and then air-dried. The garment may or may not be suitable to drying in an automatic dryer. In addition, the adhesive and receiving materials may be the same or different.

In some embodiments, the adhesive and/or receiving materials may comprise an elastomeric and/or adhesive property. In some embodiments, the material may be a skin-safe material, meaning that upon contact with human skin a negative reaction such as a rash is typically not observed after a period of time considered determinative by a health care professional (e.g., 15-30 minutes or an hour). The material may be considered by those of ordinary skill in the art to be a pressure-sensitive adhesive ("PSA"; (with or without tackifier as described below). Suitable, exemplary compositions and/or methods for making the same are described in any one or more of U.S. Pat. Nos. 4,140,115A; 4,693,776A; 4,732,808A; 5,133,970A; 5,296,512A; 5,296,625; 5,306,504A; 5,543,151A; 5,739,371; 5,876,855A; 5,891,957A; 5,908,949; 6,036,577A; 6,087,522; 6,177,482B1; 6,191,189B1; 6,198,016B1; 6,211,263B1; 6,316,524B1; 6,369,126B1; 6,660,901B2; and/or US 2005/0282977A1, for instance. The material may be of any suitable character including but not limited to hydrophobic, siliphilic, and/or oleophilic. In some embodiments, the elastomer may comprise silicon (e.g., a composition comprising silicon (Si), such as silicon dioxide ($SiO_2$), such as a silicon-based elastomer) and/or a polyurethane (e.g., a polyurethane-based elastomer). Suitable exemplary compositions including silicon or silocone and/or methods for making the same are described in, for instance, U.S. Pat. Nos. 3,527,655A; 3,669,072A; 3,794,556A; 3,892,707A; 3,989,668A; 4,157,357A; 4,831,070; 4,882,377A; 4,991,574; 6,200,195B1; 6,479,724B1; US 2002/0193723A1; US 2009/0068475A1, for instance. In some embodiments, the adhesive may comprise a silicon or silicone-based adhesive and/or a polyurethane (e.g., a polyurethane-based adhesive). In some embodiments, the material may comprise an elastomer or adhesive prepared using a catalyst. Thus, in some embodiments, the material may comprise a platinum (Pt)-catalyzed silicone-containing elastomer including, but not limited to, one and two-part elastomers curing with or without the application of heat. In some embodiments, a two-component, room temperature vulcanizing (RTV) (heat not required), platinum (Pt)-catalyzed, addition cure silicone rubber system capable of accepting additives to carefully control speed of cure, degree of adhesion, and levels of elasticity may be used. In some preferred embodiments, the elastomer may be a two-part (e.g., "Part A" and "Part B", Part B being the catalyst) Pt-catalyzed system may include a weight or volume ratio of one part Part A to ten parts Parts B (1A:10B) as well as 1A:1B. Exemplary Part A and B silicones may be, for instance, organo-functional siloxane liquids with cross-linkers (Part A) and catalysts (Part B) separated before mixing to prevent curing. In some preferred embodiments, the system cures in the range of a Shore A10 to Shore OO30 (before tackifier addition, if present in the composition).

In some preferred embodiments, a tackifier may be combined with the Part A/Part B system. In preferred embodiments, the optimized range of the tackifier additive may be one part mixed silicone rubber (including the mixture of Parts A and B such as that described above) to 1.25 to 1.75 parts tackifier (1:1.25-1.75 by weight or volume) depending upon which initial Shore hardness silicone is used. Suitable tackifiers include any of those available to those of ordinary skill in the art, including but not limited to compounds of modest molecular weight, glass transition and softening temperatures above room temperature, and viscoelastic properties. An exemplary tackifier is a silicone-based chain extender.

In some embodiments, a composition may be applied to surface upon which the compression garment is to be attached to enhance adhesion thereto (such as those described in, e.g., U.S. Pat. Nos. 6,177,482B1; 6,211,263B1; and/or 6,369,126B1). In preferred embodiments, the device described herein comprises the Part A/Part B elastomer composition lacking tackifier on the device surface that, in use, is not immediately adjacent to (i.e., making contact with) the skin and the tackified composition is present on the opposite surface of the device (i.e., the surface contacting the skin). Thus, a first surface of the device may comprise a mixture of the Part A/Part B elastomer and tackifier (e.g., the adhesive material), and the other may comprise only the Part A/Part B elastomer (i.e., lack the tackifier; e.g., the receiving material). Other embodiments of suitable adhesive and/or receiving materials are also contemplated as would be understood by those of ordinary skill in the art.

The adhesive and/or receiving materials may be present on the support material in a variety of thicknesses (e.g., as measured in either direction, or both directions, from the support material) and orientations. For instance, the adhesive and/or receiving materials may be present and/or applied as a "layer" of any appropriate thickness (e.g., about any of 1, 2, 3, 4, or 5 mm). The term "layer", as used herein, does not necessarily mean a coating of adhesive and/or receiving material that is separate from the support material since, as described above, the support material may be a single, open mesh, breathable, stretchable, elastomeric fabric substrate (e.g., Spandex, Lycra, nylon and/or the like) bonded to (e.g., directly) and/or encapsulated by the adhesive and/or receiving material, thereby providing a single "layered" compression garment that includes the adhesive and/or receiving material and the support material. In some embodiments, adhesive material may be coated or "layered" onto receiving material and vice-versa. The sections of the compression garment including the adhesive and/or receiving material may be of any appropriate width (e.g., extending from an edge toward the central axis about 1, 5, 10, 15, 20 or 25% of the distance between the two). In a compression garment with multiple edges having adhesive and/or receiving materials, the thickness and/or width of the section including the adhesive and/or receiving materials may be same or different on each edge thereof. One or both sides (e.g., surface attached to the skin and the surface not contacting the skin) of the support material may comprise adhesive and/or receiving materials, and each side may comprise the same and/or different adhesive and/or receiving materials in the same and/or different thickness, width and/or type of adhesive and/or receiving materials.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

A body part may be a limb and may include any appendage of a subject such as but not limited to an arm, hand, finger, leg, thigh, knee, calf, foot, and/or any portion thereof.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

The term "combined" or "in combination" or "in conjunction" may refer to a physical combination of agents that are administered together or the use of two or more agents in a regimen (e.g., administered separately, physically and/or in time) for treating, preventing and/or ameliorating a particular disease.

When the terms treat, prevent, and/or ameliorate or derivatives thereof are used herein in connection with a given treatment for a given condition (e.g., preventing cancer infection by HIV), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected. For instance, a treatment can "prevent" infection by resulting in the patient's displaying only mild overt symptoms of the infection; it does not imply that there must have been no penetration of any cell by the infecting microorganism.

Similarly, reduce, reducing, and reduction as used herein in connection with prevention, treatment and / or amelioration of a given condition by a particular treatment typically refers to a subject developing an infection more slowly or to a lesser degree as compared to a control or basal level of developing an infection in the absence of a treatment.

All references cited within this disclosure are hereby incorporated by reference into this application in their entirety. Certain embodiments are further described in the following examples. These embodiments are provided as examples only and are not intended to limit the scope of the claims in any way.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A compression garment comprising:
a support material having a central axis,
first and second surfaces opposite one another,
at least one first edge and at least one second edge on each surface wherein the edges may be the same or different on each surface,
at least first edges comprises an adhesive material on the first or second surface thereof, said adhesive material extending toward the central axis; and,
at least one second edge comprises a receiving material extending from the second edge toward the central axis; wherein:
said receiving material adheres to the adhesive material;
the first edge comprising the adhesive material is opposite relative to the central axis as the second edge comprising the receiving material;
the first edge comprising the adhesive material is on the first surface and the second edge comprising the receiving material is on the second surface;
the compression garment comprises at least one edge does not comprise adhesive and/or receiving material;
the adhesive and/or receiving materials are present on the first surface, the second surface, or the first and second surfaces;
the support material comprises at least two sections comprising adhesive and/or receiving material and comprises at least two sections lacking adhesive and/or receiving material:
the compression garment comprises multiple edges wherein at least one edge comprises a semi-rigid/rigid support; and/or,
the adhesive and/or receiving materials are skin-safe, comprise an elastomer, comprise a silicone-based elastomer or silicone-based adhesive, comprise a platinum-catalyzed silicone-containing elastomer, and/or comprise a polyurethane-based elastomer or polyurethane-based adhesive.

2. The compression garment of claim 1 wherein the adhesive material and the receiving material are different or the same.

3. The compression garment of claim 1 wherein the elastomer is formed from a mixture of one or more organofunctional siloxane liquids and cross-linkers with one or more catalysts.

4. The compression garment of any one of claim 1 wherein the either or both of the adhesive and/or receiving materials comprises a tackifier.

5. The compression garment of claim 4 wherein the tackifier is a silicone-based chain extender.

6. The compression garment of claim 4 wherein the adhesive and/or receiving material comprises an elastomer and at least one tackifier is present in the adhesive and/or receiving material mixture at an elastomer:tackifier ratio of 1:1.25-1.75 by weight or volume.

7. The compression garment of claim 4 wherein the adhesive material comprises a tackifier and the receiving material does not comprise a tackifier.

8. The compression garment of claim 1, wherein the adhesive and receiving materials are stable upon contact with an aqueous solution.

9. The compression garment of claim 8 wherein the aqueous solution is water or sweat.

10. The compression garment of claim 1, wherein the support material comprises stretch characteristics; a textile material; a compressible material; a non-compressible material; an elastic material; an inelastic material; elastic compression threads; elastomeric loop material, elastomeric fabric; a semi-compressible elastomeric material; woven material; non-woven material; a rhombic lattice pattern; longitudinal yams arranged to form a fabric having a length and generally parellel to the length, and a plurality of transverse elastomeric yarns the longitudinal yarns where, in a stretched state, the longintudinal yarns are spaced from one another and remain generally parallel to the length; a seamlessly attached antislip coating along one or more edges; breathable material; breathable short stretch foam laminate material; a wicking layer; measurement indicia; pressure indicia; an arrangement of materials to provide graduated compression along its length; padding; a compressible or semi-compressible liner; a medicinal agent, a therapeutic agent, or a medicinal agent and a therapeutic agent; and/or an inner and outer compressible and/or non-compressible layer upon either or both of which is a compressible layer.

11. The compression garment of claim 10 wherein the garment may be secured to a limb using the adhesive and receiving materials.

12. A kit comprising a compression garment of any one of claim 1.

13. A method for compressing a limb, the method comprising wrapping the compression garment of claim 1 around the limb to apply pressure thereupon, wherein the compression garment is secured to the limb by contacting the adhesive and receiving materials to secure the compression garment to the limb.

14. The method of claim 13 wherein the garment provides a user-selected amount of pressure to the limb.

* * * * *